(12) United States Patent
Wing-Chiu et al.

(10) Patent No.: US 6,448,441 B1
(45) Date of Patent: Sep. 10, 2002

(54) GASIFICATION PROCESS FOR AMMONIA/ UREA PRODUCTION

(75) Inventors: Francis Fong Wing-Chiu, Yorktown Heights, NY (US); Erwin A. Reich, Stamford, CT (US)

(73) Assignee: Texaco, Inc., White Plains, NY (US)

( * ) Notice: Subject to any disclaimer, the term of this patent is extended or adjusted under 35 U.S.C. 154(b) by 0 days.

(21) Appl. No.: 09/850,480

(22) Filed: May 7, 2001

(51) Int. Cl.$^7$ ................. C07C 273/10; C07C 273/04
(52) U.S. Cl. .................... 564/67; 564/69; 564/70; 564/72
(58) Field of Search ............... 564/67, 69, 70, 564/72

(56) References Cited

U.S. PATENT DOCUMENTS

| | | | |
|---|---|---|---|
| 4,213,957 A | 7/1980 | Pinto | 423/359 |
| 4,524,056 A | 6/1985 | Banquy | 423/359 |
| 4,869,887 A | 9/1989 | Van Dijk | 423/359 |
| 5,900,224 A | 5/1999 | Fujimura et al. | 423/359 |
| 5,980,858 A | 11/1999 | Fujimura et al. | 423/655 |
| 6,063,355 A | 5/2000 | Fujimura et al. | 423/359 |

*Primary Examiner*—Peter O'Sullivan
(74) *Attorney, Agent, or Firm*—Howrey Simon Arnold & White LLP

(57) ABSTRACT

The present invention involves a process for the co-production of ammonia and urea in which two parallel gasifiers are utilized so as to optimize the $H_2/CO_2$ ratio in the combined syngas product, thereby maximizing the ammonia and urea production. In a first gasifier, solid and/or liquid hydrocarbon materials are partially oxidized in the presence of an oxygen-rich gas in the presence of a temperature moderator, thereby generating a first synthesis gas mixture comprising carbon monoxide, hydrogen and carbon dioxide. In a second gasifier, natural gas is partially oxidized in the presence of an oxygen-rich gas, thereby generating a first synthesis gas mixture comprising carbon monoxide, hydrogen and carbon dioxide. Because natural gas has a lower C/H ratio than the solid and/or liquid hydrocarbon materials, insufficient $CO_2$ is produced in the natural gas gasifier for urea production when only natural gas is used to produce syngas. Conversely, the high C/H ratio of the solid and/or liquid hydrocarbon materials produces an excess amount of $CO_2$-much more than is needed for urea production-and thus a large portion of the $CO_2$ is vented when only solid and/or liquid hydrocarbon materials are used to produce syngas. By running two gasifiers in parallel on the separate feeds, the feedrate to each gasfier can be adjusted to optimize to maximize the $H_2/CO_2$ ratio in the combined syngas product stream, resulting in an elimination or minimization of $CO_2$ emissions from the integrated gasification, ammonia and urea production facility.

17 Claims, 2 Drawing Sheets

GASIFICATION PROCESS FOR AMMONIA/UREA PRODUCTION

BACKGROUND OF THE INVENTION

In the production of ammonia ($NH_3$) and urea (($NH_2)_2CO$), a syngas feedstream comprising hydrogen ($H_2$) and carbon monoxide (CO) is first fed to a CO shift unit to convert CO to $CO_2$, before being routed to an acid gas removal facility where the $CO_2$ is separated from the $H_2$. The $H_2$ is then combined with nitrogen ($N_2$) and fed to an ammonia synthesis unit. The $CO_2$ is then combined with a portion of the $NH_3$ product and fed to an urea synthesis unit. The primary reactions of this process are:

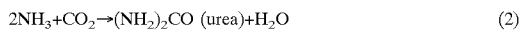

$$3H_2 + N2 \rightarrow 2NH_3 \text{ (ammonia)} \qquad (1)$$

$$2NH_3 + CO_2 \rightarrow (NH_2)_2CO \text{ (urea)} + H_2O \qquad (2)$$

It is known to use gasification to produce the syngas feed to an ammonia/urea production facility. In the gasification process, hydrocarbonaceous material is partially oxidized in the presence of an oxygen rich gas and a temperature moderator at high temperatures. The syngas product of the gasification process primarily comprises $H_2$ and CO. There are many different types of hydrocarbonaceous material that can be fed to a gasification reactor, from natural gas to heavy oils and solid materials such as coal. Because natural gas has a lower C/H ratio than solid and liquid hydrocarbon materials, insufficient $CO_2$ is produced for urea production when a natural gas gasifier is used to produce syngas. Conversely, the high C/H ratio of solid and liquid hydrocarbon materials produces an excess amount of $CO_2$-much more than is needed for urea production-and thus a large portion of the $CO_2$ is vented when only solid and/or liquid hydrocarbon materials are used to produce syngas. Thus, it would be beneficial to develop an integrated gasification and ammonia/urea production process that optimizes the $CO_2$ content of the syngas so as to maximize urea production. Furthermore, $CO_2$ is known to have an adverse effect on the environment, such as contributing to global warming, so it would also be desirable to minimize $CO_2$ venting in an integrated gasification/urea production facility.

SUMMARY OF THE INVENTION

The present invention involves a process for the co-production of ammonia and urea in which two parallel gasifiers are utilized so as to optimize the $H_2/CO_2$ ratio in the combined syngas product, thereby maximizing the ammonia and urea production. In a first gasifier, solid and/or liquid hydrocarbon materials are partially oxidized in the presence of an oxygen-rich gas in the presence of a temperature moderator, thereby generating a first synthesis gas mixture comprising carbon monoxide, hydrogen and carbon dioxide. The oxygen-rich gas is normally extracted from air through an air separation unit (ASU). The by-product of the ASU, nitrogen ($N_2$), is used in the downstream ammonia production unit.

In a second gasifier, natural gas is partially oxidized in the presence of an oxygen-rich gas, thereby generating a first synthesis gas mixture comprising carbon monoxide, hydrogen and carbon dioxide. By running two gasifiers in parallel on the separate feeds, the feedrates to each gasfier can be independently adjusted to optimize the $H_2/CO_2$ ratio in the combined syngas product stream, thus maximizing ammonia and urea production and minimizing $CO_2$ emissions.

The combined syngas product stream is then processed in a CO shift reactor so as to convert any CO in the syngas into $H_2$ and $CO_2$. The $CO_2$ is then removed from the syngas, usually along with $H_2S$ and any other sulfur components in an acid gas removal unit, leaving a substantially pure $H_2$ stream. The $H_2$ stream is then combined with $N_2$ from the air separation unit to form ammonia ($NH_3$). The $CO_2$ recovered from a CO2 recovery unit is combined with at least a portion of the $NH_3$ product to form urea (($NH_2)_2CO$).

DESCRIPTION OF ILLUSTRATIVE EMBODIMENTS

Figure 1:
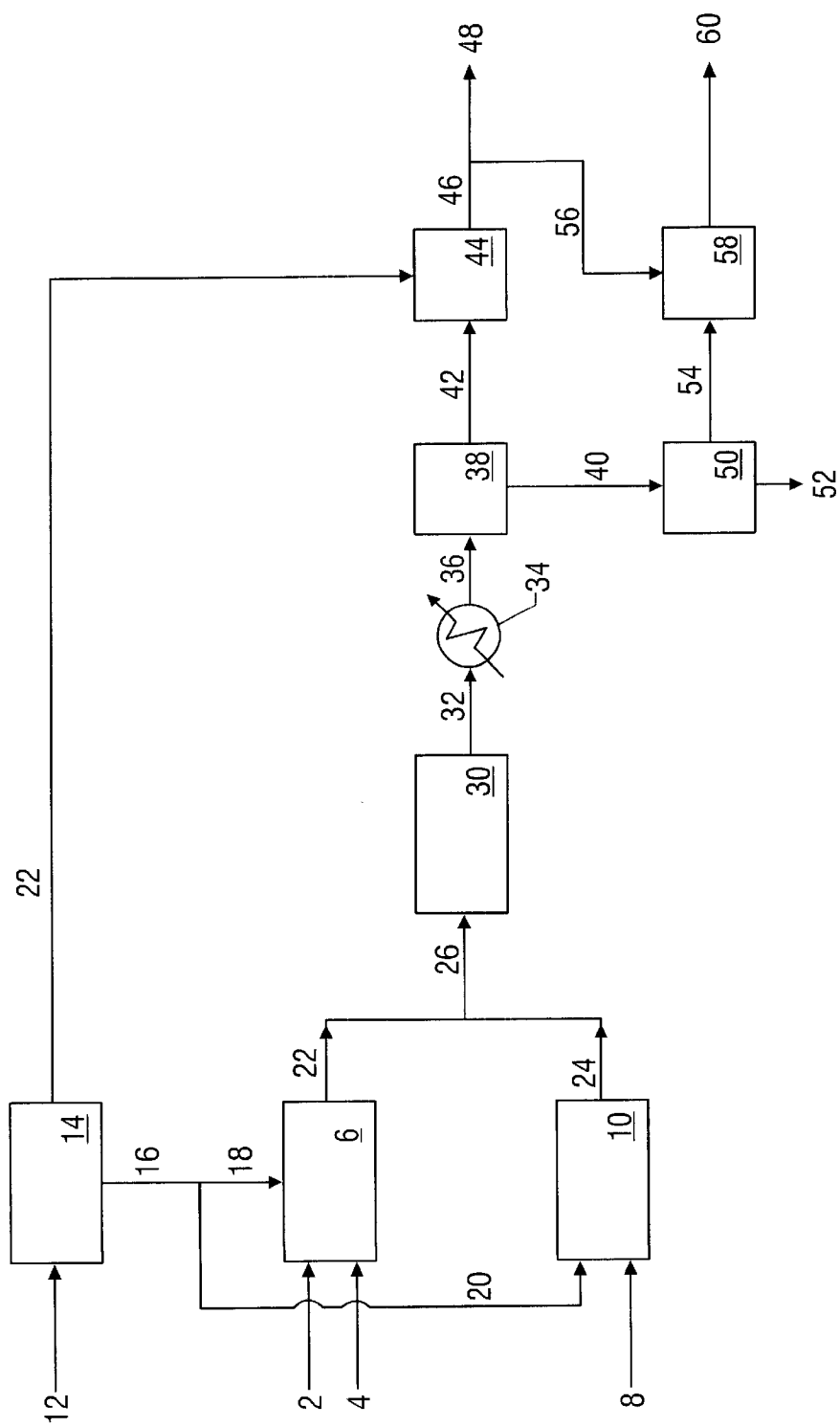
FIG. 1 is an illustration of one embodiment of the present invention, in which a solid and/or liquid gasifier is run in parallel with a natural gas gasifier to form an optimized syngas product.

In the instant invention, carbonaceous fuel is first obtained and prepared for feeding to a gasification reactor. Carbonaceous fuel is any solid, liquid, or gaseous combustible organic material that can be used as feedstock to a gasification process for produce synthesis gas production. The feedstock for a gasification process is usually a hydrocarbonaceous material, that is, one or more materials, generally organic, which comprises elements of hydrogen and carbon for the gasification reaction. The hydrocarbonaceous material can be in a gaseous, liquid or solid state, or in a combination as desired, for example, a solid-liquid composition in a fluidized state.

The feed preparation step may not be necessary, given the composition and physical nature of the feedstock. Generally, solid carbonaceous fuels will need to be liquefied with oil or water prior to feeding to the gasifier. Liquid and gaseous carbonaceous fuels may be suitable for direct feed to the gasifier, but can be pre-treated for removal of any impurities that might be present in the feed.

The term liquid hydrocarbonaceous fuel as used herein to describe various suitable feedstocks is intended to include pumpable liquid hydrocarbon materials and pumpable liquid slurries of solid carbonaceous materials, and mixtures thereof. For example, pumpable aqueous slurries of solid carbonaceous fuels are suitable feedstocks. In fact, substantially any combustible carbon-containing liquid organic material, or slurries thereof may be included within the definition of the term "liquid hydrocarbonaceous." For example, there are:

(1) pumpable slurries of solid carbonaceous fuels, such as coal, particulate carbon, petroleum coke, concentrated sewer sludge, and mixtures thereof, in a vaporizable liquid carrier, such as water, liquid $CO_2$, liquid hydrocarbon fuel, and mixtures thereof;

(2) suitable liquid hydrocarbon fuel feedstocks to the gasifier, is intended to include various materials, such as liquefied petroleum gas, petroleum distillates and residua, gasoline, naphtha, kerosine, crude petroleum, asphalt, gas oil, residual oil, tar sand oil and shale oil, coal derived oil, aromatic hydrocarbons (such as benzene, toluene, xylene fractions), coal tar, cycle gas oil from fluid-catalytic-cracking operations, furfural extract of coker gas oil, and mixtures thereof;

(3) also included within the definition of the term liquid hydrocarbonaceous are oxygenated hydrocarbonaceous organic materials including carbohydrates, cellulosic materials, aldehydes, organic acids, alcohols, ketones, oxygenated fuel oil, waste liquids and by-products from chemical processes containing oxygenated hydrocarbonaceous organic materials, and mixtures thereof.

Gaseous hydrocarbonaceous fuels that may be burned in the partial oxidation gasifier alone or along with the liquid hydrocarbonaceous fuel includes vaporized liquid natural gas, refinery off-gas, $C_1$–$C_4$ hydrocarbonaceous gases, and waste carbon-containing gases from chemical processes.

After the feed preparation step, if used, the solid and/or liquid carbonaceous fuel is sent to a first gasification reactor, or gasifier, and natural gas is sent to a second gasifier. In each gasifier, the feed is reacted with a reactive free oxygen-containing gas. The term free-oxygen containing gas as used herein means air, oxygen-enriched air i.e. greater than 21 mole % $O_2$, and substantially pure oxygen, i.e. greater than about 95% mole oxygen (the remainder usually comprising $N_2$ and rare gases). Substantially pure oxygen is preferred, such as that which is produced by an air separation unit (ASU). The partial oxidation of the hydrocarbonaceous material is completed, advantageously in the presence of a temperature control moderator such as steam, in a gasification zone to obtain hot synthesis gas, or syngas. Syngas and synthesis gas can and are used interchangeably throughout this specification.

The need for a temperature moderator to control the temperature in the reaction zone of the gas generator depends in general on the carbon-to-hydrogen ratios of the feedstock and the oxygen content of the oxidant stream. A temperature moderator is commonly used with liquid hydrocarbon fuels with substantially pure oxygen. Water or steam are the preferred temperature moderators. Steam may be introduced as a temperature moderator in admixture with either or both reactant streams. Alternatively, the temperature moderator may be introduced into the reaction zone of the gas generator by way of a separate conduit in the burner. Other temperature moderators include $CO_2$-rich gas, nitrogen, and recycled synthesis gas.

A gasification reactor generally comprises a reaction zone, made up of a vertical cylindrically shaped steel pressure vessel lined with refractory, and a quench drum, such as shown in U.S. Pat. No. 2,809,104, which is incorporated herein by reference. A burner, such as shown in U.S. Pat. No. 2,928,460, which is incorporated herein by reference, may be used to introduce the feed streams into the reaction zone. In the reaction zone of a gasifier, the contents will commonly reach temperatures in the range of about 1,700° F. (927° C.) to 3,000° F. (1649° C.), and more typically in the range of about 2,000° F. (1093° C.) to 2,800° F. (1538° C.). Pressure will typically be in the range of about 1 psi (101 kPa) to about 3675 psi (25,331 kPa), and more typically in the range of about 200 psi (1378 kPa) to about 2000 psi (13,782 kPa), and even more typically in the range of about 800 psi (5513 kPa) to about 1200 psi (8269 kPa). See U.S. Pat. No. 3,945,942 describing a partial oxidation burner assembly. See U.S. Pat. No. 5,656,044 describing a method and an apparatus for the gasification of organic materials. See also U.S. Pat. Nos. 5,435,940, 4,851,013, and 4,159,238 describing a few of the many gasification processes known in the prior art. The entire disclosures of the above referenced patents are hereby incorporated by reference and relied upon.

The hot gasification process product synthesis gas, or syngas, comprises carbon monoxide, carbon dioxide, and hydrogen. Other materials often found in the synthesis gas include hydrogen sulfide, ammonia, cyanides, and particulates in the form of carbon and trace metals. The extent of the contaminants in the feed is determined by the type of feed and the particular gasification process utilized as well as the operating conditions. In any event, the removal of these contaminants is preferable to make gasification a viable process.

As the synthesis gas is discharged from the gasifier, it passes into the gasificcation quench chamber for cleaning. The turbulent condition in the quench drum, caused by large volumes of gases bubbling up through the water helps the water to scrub much of the solids from the effluent gas. Large quantities of steam are generated within the quench vessel and saturate the syngas stream. The stream of raw gas is cooled in the quench drum and leaves at a temperature in the range of about 350° F. to 600° F. (about 175° C. to 315° C.), such as about 450° F. to 550° F. (about 230° C. to 290° C.), and a pressure in the range of about 500 to 2500 psia, such as about 1000 psia. Advantageously, fresh quench water is a mixture of make-up water and condensate produced subsequently in the process.

After the gasification step, the syngas from the solid and/or liquid hydrocarbon gasifier and the syngas from the natural gas gasifier are combined. The combined synthesis gas stream may then be advantageously shifted with steam to convert CO in the synthesis gas to carbon dioxide ($CO_2$) and hydrogen ($H_2$) by way of the water gas shift reaction to optimize the $H_2/CO_2$ ratio for use in the downstream ammonia and urea synthesis units. The synthesis gas from the gasifier is shifted using steam and a suitable catalyst to form hydrogen and carbon dioxide as shown below:

$$H_2O + CO \rightarrow H_2 + CO_2 \tag{3}$$

About 90–98% of the CO is converted to $H_2$ and $CO_2$ in the shift reactor. Methods and apparatuses to carry out the shift reaction are known in the art, and one of ordinary skill in the art will be able to select the appropriate means for accomplishing this step.

After being discharged from the shift unit, the synthesis gas is sent to an acid gas removal unit so that the impurities in the syngas can be removed. The acid gas removal facilities for the synthesis gas, usually employing amine or physical solvents, removes the acid gases, particularly the carbon dioxide and hydrogen sulfide, from the synthesis gas stream. The acid gas removal facilities typically operate at low temperatures. After the synthesis gas is cooled to below about 130° F. (54° C.), preferably below about 100° F. (38° C.), the contaminants in the gas, especially sulfur compounds and acid gases, are readily removed. The synthesis gas is contacted with the solvent in an acid gas removal contactor. The contactor may be of any type known to the art, including trays or a packed column, and operation of such an acid removal contactor is also known in the art. The acid gas stream is then sent to a carbon dioxide recovery unit, where hydrogen sulfide is removed from the $CO_2$ and commonly routed to a sulfur recovery process, with the recovered carbon dioxide being sent to the downstream urea synthesis unit.

The purified synthesis gas, now comprising mostly hydrogen, is sent to an ammonia synthesis unit. As embodied herein, any process for ammonia synthesis may be used. The most common industrial process for ammonia synthesis involves forming a mixture of gaseous nitrogen and hydrogen in a 1 to 3 molar ratio, and is reacted in accordance with the following equation:

$$3H_2 + N_2 \rightarrow 2NH_3 \tag{4}$$

This gas mixture is then compressed to high pressure (from about 80 bar to about 220 bar), heated (from about 450° C.

to about 550° C.) and passed over a catalyst where ammonia formation occurs. During ammonia synthesis, the reactants (nitrogen and hydrogen) and the product (ammonia) are in equilibrium, so, to increase the total amount of ammonia formed, the equilibrium should be shifted to product formation by removing ammonia from the reaction mixture as it is produced.

Removal of the ammonia is usually accomplished by cooling the gas mixture to a relatively low temperature (about −5° C. to about 25° C.). In this temperature range, a two-phase mixture is formed with ammonia being a liquid and nitrogen and hydrogen remaining as gases. The liquefied ammonia is separated from the other components of the mixture, and the remaining nitrogen and hydrogen are subsequently re-heated to the operating temperature for ammonia conversion and passed through the reactor again. Distillation and single-stage flash are other methods that have been used to separate ammonia from a synthesis gas.

A portion of the ammonia product is then combined with the $CO_2$ removed from the syngas and sent to a urea production unit. As embodied herein, any process for urea synthesis may be used. In a common urea synthesis process, the ammonia and carbon dioxide are fed into the synthesis section to form ammonium carbamate in accordance with the exothermic reaction:

$$2NH_3 + CO_2 \leftrightarrows NH_2COONH_4 \qquad (5)$$

A fraction of the ammonium carbamate then dehydrates to form urea and water in accordance with the endothermic reversible reaction:

$$NH_2COONH_4 \leftrightarrows (NH_2)_2CO + H_2O \qquad (6)$$

Under the normally used synthesis conditions, i.e., pressures of between about 120 and 300 bars and temperatures between about 170° C. and 250° C., the carbamate formation reaction is extremely fast and practically complete, whereas the dehydration reaction proceeds slowly towards equilibrium. That fraction of the ammonium carbamate which dehydrates to form urea is determined not only by the reaction temperature and pressure but also by the ratio of the various reactants and the residence time in the synthesis section. The molar ratios normally used are: ammonia/carbon dioxide: from 2.5 to 7; and water/carbon dioxide: from 0 to 1. Water is present both as reaction product and a component of any recycle streams from the plant sections downstream of the synthesis section. The residence time in the synthesis section varies from 20 to 90 minutes.

The product of the synthesis reaction consists substantially of a solution comprising ammonium carbamate, urea, water and free ammonia, in that all the industrially used processes operate with a substantial excess of ammonia to obtain high yields and limit the formation of harmful by-products such as biuret. The free ammonia and the ammonium carbamate are separated from the urea solution obtained from the synthesis section and recycled to the synthesis section for their complete conversion into urea. The urea solution then has to be further processed to obtain the granular product in accordance with current commercial specifications. The various industrial urea production processes are characterized precisely by their methods for separating and recycling those components not converted to urea. Any known process may be used as the urea production unit of the present invention.

Referring now to FIG. 1, the first embodiment of the present invention is illustrated in schematic form. Solid or liquid hydrocarbonaceous feed 2 is fed to a first gasification reactor 6 along with a temperature moderator 4 and oxygen 18. Natural gas feed 8 is fed to a second gasification reactor 10 along with oxygen 20. Oxygen 18 and oxygen 20 are produced from an air separation unit 14 which separates air 12 into oxygen 16 and nitrogen 22. The syngas products 22 and 24 from the first gasification reactor 6 and the second gasification reactor 10, respectively, are combined into syngas stream 26. The feedrates to each gasification reactor are independently adjusted so as to optimize the composition of the syngas stream 26. For instance, if a higher $CO_2$ content in syngas stream 26 is desired, the feedrate to the first gasification reactor 6 would be increased, or the feedrate to the second gasification reactor 10 would be decreased. The syngas stream 26 is then sent to a shift unit 30, where a substantial portion of the CO present in the syngas stream 26 is converted into $CO_2$ and $H_2$.

The shifted syngas 32 is then cooled in exchanger 34 and processed in acid gas removal unit 38. In acid gas removal unit 38, the $CO_2$ is separated from the $H_2$ in the syngas. The $CO_2$ is removed via line 40, along with any sulfur compounds present in the shifted syngas stream 36. The remaining $H_2$ stream 42 is then combined with nitrogen stream 22 from air separation unit 14 and sent to ammonia synthesis reactor 44. The ammonia product 46 is recovered and either sent to urea reactor 58 or removed for use in other processes via line 48.

$CO_2$ waste stream 40 is then sent to a $CO_2$ recovery unit 50 where a substantially pure stream of $CO_2$ 54 is recovered, leaving a waste stream 52. The $CO_2$ stream 54 is combined with ammonia stream 56 and sent to urea reactor 58. Finally, urea product 60 is obtained from the urea reactor 58 and is thus sent to storage or to other downstream processes. Depending on the desired amount of ammonia production 48 and urea production 60, the feedstreams 2 and 8 to gasifiers 6 and 10, respectively, are independently adjusted.

In a second embodiment, only natural gas is used as a feedstock to the ammonia/urea production unit. Natural gas can be gasified, as describe above, or can be processed in a steam-methane reforming process. As embodied herein, any known steam-methane reforming process may be used. In a common steam-methane reforming (SMR) process natural gas is heated to about 750° F., and any $H_2S$ is removed using a solid adsorbent, typically zinc oxide (ZnO). Process steam is mixed with the natural gas resulting in a mixed feed with a steam/carbon ratio of 1.0–3.5 (typically 1.5). Carbon dioxide, if available, can also be mixed into the feed from 0.1 to 2.0 $CO_2/C$ ratios. The mixed feed (steam and natural gas) is heated in a convection section coil to about 900° F. to 1050° F. and enters a SMR. In the SMR, the mixed feed passes through tubes with a Ni containing catalyst, such as 5–30% Ni on an alumina support, which promotes the reaction of methane and steam to produce hydrogen and carbon monoxide, the reforming reaction, following the following formula:

$$CH_4 + H_2O \rightarrow 3H_2 + CO \qquad (7)$$

The water gas reaction, illustrated by the following formula:

$$CO + H_2O \rightarrow CO_2 + H_2 \qquad (8)$$

also occurs to yield a synthesis gas containing hydrogen, carbon monoxide, carbon dioxide, water and small amounts of unreacted methane. The synthesis gas exits the SMR at about 1300° F. to 1700° F. The final syngas product contains about 70 to 72 mole percent hydrogen, 6 to 8 percent unconverted methane, 8 to 10 percent carbon dioxide, and 10 to 14 percent carbon monoxide, all on a dry basis.

The remaining steps are substantially the same as outlined above in the previous embodiment. The synthesis gas is shifted, the $CO_2$ and other impurities are removed, the $H_2$ is reacted with $N_2$ to form ammonia, and the $CO_2$ is reacted with a portion of the ammonia to form urea. Because the gasification of natural gas does not produce enough carbon dioxide for maximum urea production, a carbon dioxide generation process is used to provide makeup $CO_2$ to the urea synthesis process. As embodied herein, any process for carbon dioxide synthesis may be used.

The most common preparation of carbon dioxide generally involves the steps of crude gas generation, purification and separation. Generation of crude carbon dioxide involves the combustion of liquid fuels such as fuel oil, or solid fuels such as anthracites, coke, charcoal, and the like, with excess air to promote complete oxidation of the fuel and to provide a carbon dioxide rich combustion exhaust gas. Purification of the combustion exhaust gas generally involves several separate treatments to provide a gas having high purity. These purification treatments include washing, absorption, adsorption, desorption, and the removal of reducing substances. Washing generally involves a water absorption shower (water wash) to remove solids (soot, carried off ashes, etc.) and at the same time to cool the combustion gases. Various scrubbing solutions are generally employed to remove contaminants and to reduce the components in the combustion gas mixture to carbon dioxide, nitrogen, and oxygen. The combustion exhaust gas may also be passed through a tower containing a recirculating oxidizing solution such as potassium permanganate to remove traces of organic impurities carried with the gas.

The washed and scrubbed combustion gas is then separated to obtain a carbon dioxide rich fraction. In one separation method, the combustion gas mixture is circulated through a counter-current shower of an absorbing solution such as potassium carbonate, monoethanol-amine, and the like. Carbon dioxide can be desorbed by heating the carbon dioxide saturated solution to a temperature above 100° C. In another separation method, the combustion mixture is separated by selectively adsorbing the carbon dioxide on a zeolite bed in a pressure swing adsorption system. The most common methods for separating nitrogen from air are cryogenic fractional distillation, inert gas generation (combustion of natural gas or propane in air), and pressure swing adsorption, all of which are known in the art.

The supplemental carbon dioxide is then combined with the carbon dioxide that was removed from the syngas, further combined with a portion of the ammonia product, and sent to a urea synthesis unit as outlined above.

Figure 2:
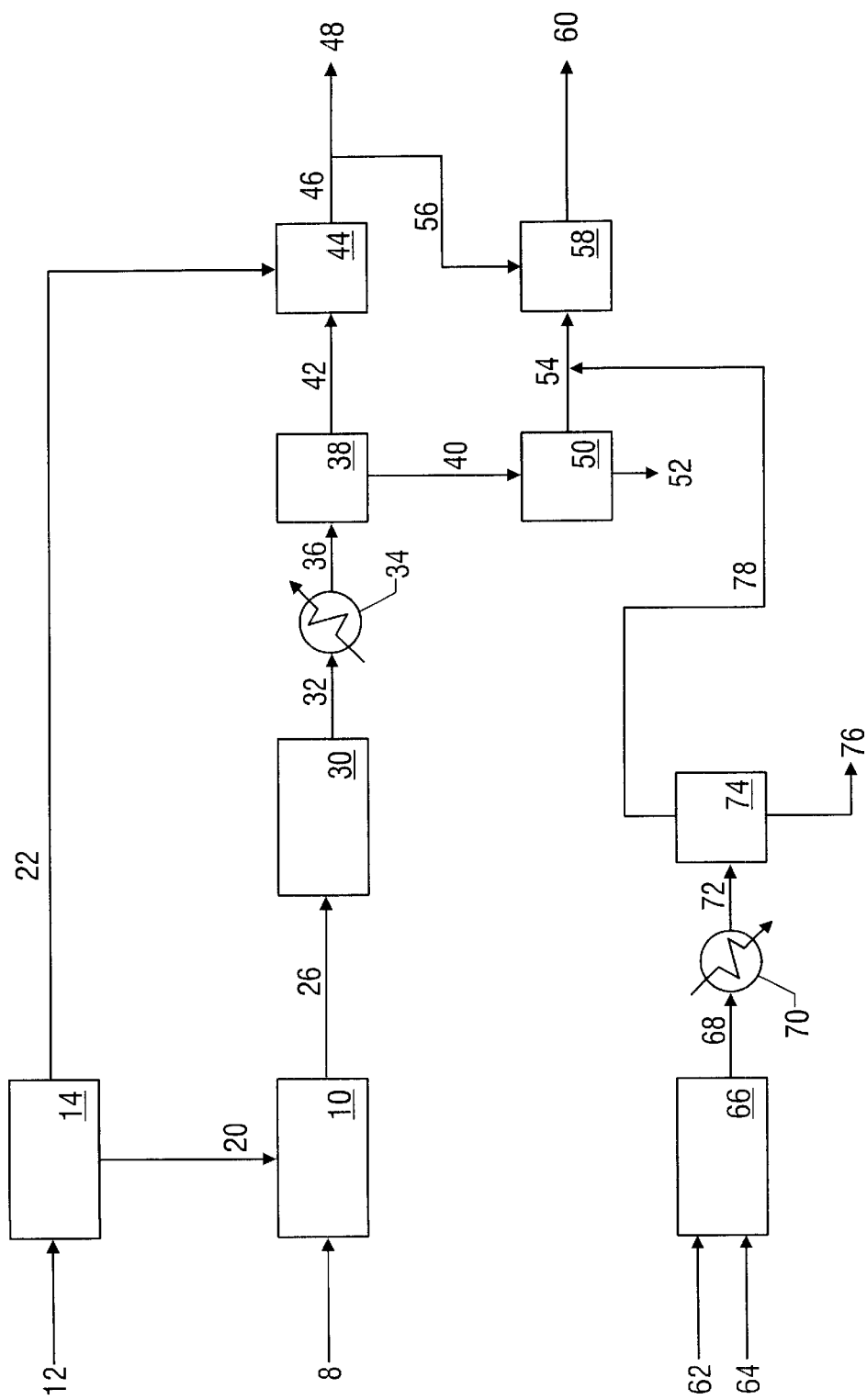
FIG. 2 is an illustration of a second embodiment of the present invention, wherein a $CO_2$ generator is used to make up the $CO_2$ deficiency in the syngas when only a natural gas gasifier is used.

Referring now to FIG. 2, a second embodiment of the present invention is illustrated in schematic form. For simplicity, units and streams FIG. 2 has in common with FIG. 1 have retained the unit or stream number from FIG. 1. Natural gas feed 8 is fed to a gasification reactor 10 along with oxygen 20. Oxygen 20 is produced from an air separation unit 14 which separates air 12 into oxygen 20 and nitrogen 22. The syngas product 26 is then sent to a shift unit 30, where a substantial portion of the CO present in the syngas stream 26 is converted into $CO_2$.

The shifted syngas 32 is then cooled in exchanger 34 and processed in acid gas unit 38. In acid gas unit 38, the $CO_2$ is separated from the $H_2$ in the syngas. The $CO_2$ is removed via line 40, along with any sulfur compounds present in the shifted syngas stream 36. The remaining $H_2$ stream 42 is then combined with nitrogen stream 22 from air separation unit 14 and sent to ammonia synthesis reactor 44. The ammonia product 46 is recovered and either sent to urea reactor 58 or removed for use in other processes via line 48.

$CO_2$ waste stream 40 is then sent to a $CO_2$ recovery unit 50 where a substantially pure stream of $CO_2$ 54 is recovered, leaving a waste stream 52. The $CO_2$ recovered in stream 54 is usually not at a sufficiently high flowrate to maximize urea production. Thus, supplemental $CO_2$ 78 is added to stream 54. Supplemental $CO_2$ 78 is produced from a $CO_2$ production unit, which involves feeding a carbonaceous material 62 to a $CO_2$ generator 66 along with air 64, to produce a crude $CO_2$ stream 68. Stream 68 is then cooled in exchanger 70, and can include washing steps (not shown). The cooled steram 68 is then sent to separator 74, where condensed liquids 72 are removed from the $CO_2$ stream. The final, purified $CO_2$ product stream 78 is then combined with the $CO_2$ stream 54 that was removed from the syngas, further combined with a portion of the ammonia product 56, and sent to a urea synthesis unit 58. Finally, urea product 60 is obtained from the urea reactor 58 and is thus sent to storage or to other downstream processes.

The above illustrative embodiments are intended to serve as simplified schematic diagrams of potential embodiments of the present invention. One of ordinary skill in the art of chemical engineering should understand and appreciate that specific details of any particular embodiment may be different and will depend upon the location and needs of the system under consideration. All such layouts, schematic alternatives, and embodiments capable of achieving the present invention are considered to be within the capabilities of a person having skill in the art and thus within the scope of the present invention.

While the apparatus, compounds and methods of this invention have been described in terms of preferred embodiments, it will be apparent to those of skill in the art that variations may be applied to the process described herein without departing from the concept and scope of the invention. All such similar substitutes and modifications apparent to those skilled in the art are deemed to be within the scope and concept of the invention.

What is claimed is:

1. A process comprising:
   (a) partially oxidizing solid or liquid hydrocarbon materials, or a mixture thereof, by reacting said materials with an oxygen-rich gas in the presence of a temperature moderator, thereby generating a first synthesis gas mixture comprising carbon monoxide, hydrogen and carbon dioxide;
   (b) partially oxidizing a natural gas feed by reacting said natural gas with an oxygen-rich gas, thereby generating a second synthesis gas mixture comprising carbon monoxide, hydrogen and carbon dioxide;
   (c) combining the first synthesis gas mixture with the second synthesis gas mixture, forming a combined synthesis gas mixture comprising carbon monoxide, hydrogen and carbon dioxide;
   (d) converting a portion of the carbon monoxide in the combined synthesis gas mixture into hydrogen and carbon dioxide;
   (e) removing the carbon dioxide from the combined synthesis gas mixture, leaving a hydrogen stream;
   (f) reacting the hydrogen stream with nitrogen to form ammonia; and
   (g) reacting a portion of the ammonia with a portion of the carbon dioxide to form urea.

2. The process of claim 1 wherein the oxygen-rich gas and the nitrogen are supplied by an air separation unit.

3. The process of claim 1 wherein the combined synthesis gas mixture further comprises hydrogen sulfide.

4. The process of claim 3 further comprising removing the hydrogen sulfide from the combined synthesis gas mixture along with the carbon dioxide.

5. The process of claim 4 further comprising separating at least a portion of the carbon dioxide from the hydrogen sulfide.

6. The process of claim 5 wherein the separated carbon dioxide is reacted with the portion of the ammonia to form urea.

7. The process of claim 1 wherein the solid or liquid hydrocarbon materials are selected from the group consisting of coal and oil.

8. A process comprising:
  (a) partially oxidizing a natural gas feed by reacting said natural gas with an oxygen-rich gas, thereby generating a synthesis gas mixture comprising carbon monoxide, hydrogen and carbon dioxide;
  (b) converting a portion of the carbon monoxide in synthesis gas mixture into hydrogen and carbon dioxide;
  (c) removing the carbon dioxide from the synthesis gas mixture, leaving a hydrogen stream;
  (d) reacting the hydrogen stream with nitrogen to form ammonia;
  (e) providing a stream of makeup carbon dioxide;
  (f) combining the stream of makeup carbon dioxide with the carbon dioxide from step (c);
  (g) reacting a portion of the ammonia with the combined carbon dioxide stream from step (f) to form urea.

9. The process of claim 8 wherein the oxygen-rich gas and the nitrogen are supplied from an air separation unit.

10. The process of claim 8 wherein the synthesis gas mixture further comprises hydrogen sulfide.

11. The process of claim 10 further comprising removing the hydrogen sulfide from the synthesis gas mixture along with the carbon dioxide.

12. The process of claim 11 further comprising separating at least a portion of the carbon dioxide from the hydrogen sulfide.

13. The process of claim 12 wherein the separated carbon dioxide is combined with the makeup carbon dioxide stream in step (f) and reacted with the portion of the ammonia to form urea.

14. The process of claim 8 wherein the makeup carbon dioxide stream is supplied by a carbon dioxide generator.

15. The process of claim 14 further comprising combusting air and hydrocarbon materials in the carbon dioxide generator to form the makeup carbon dioxide stream and water.

16. The process of claim 15 further comprising cooling the makeup carbon dioxide stream and separating the makeup carbon dioxide stream and the water.

17. The process of claim 16 further comprising purifying the makeup carbon dioxide stream.

* * * * *